United States Patent [19]
Goodman, Jr. et al.

[11] Patent Number: 5,514,105
[45] Date of Patent: May 7, 1996

[54] RESILIENT PLASTIC WEB EXHIBITING REDUCED SKIN CONTACT AREA AND ENHANCED FLUID TRANSFER PROPERITES

[75] Inventors: William H. Goodman, Jr.; Donald L. Gerth, both of Cincinnati, Ohio

[73] Assignee: The Procter & Gamble Company, Cincinnati, Ohio

[21] Appl. No.: 412,634

[22] Filed: Mar. 29, 1995

Related U.S. Application Data

[63] Continuation-in-part of Ser. No. 146,675, Nov. 1, 1993, abandoned, which is a continuation-in-part of Ser. No. 817,016, Jan. 3, 1992, abandoned.

[51] Int. Cl.$^6$ .............................. A61F 13/15; A61F 13/20
[52] U.S. Cl. ...................... 604/370; 604/358; 604/366; 604/385.1; 428/137
[58] Field of Search ..................................... 604/358, 365, 604/366, 367, 370, 378, 384, 385.1; 428/137

[56] References Cited

U.S. PATENT DOCUMENTS

| | | |
|---|---|---|
| Re. 23,910 | 12/1954 | Smith et al. . |
| Re. 29,524 | 1/1978 | Spencer . |
| 691,804 | 1/1902 | Parker . |
| 2,166,366 | 7/1939 | Norris . |
| 2,776,451 | 1/1957 | Chavannes . |
| 2,809,392 | 10/1957 | Armstrong . |
| 2,816,025 | 12/1957 | Dahlberg . |
| 2,820,985 | 1/1958 | Cresswell . |
| 2,857,657 | 10/1958 | Wheeler, Jr. . |
| 2,926,490 | 3/1960 | Eaton et al. . |
| 3,054,148 | 9/1962 | Zimmerli . |
| 3,123,446 | 3/1964 | Wheeler, Jr. . |
| 3,174,837 | 3/1965 | Mears . |
| 3,312,583 | 4/1967 | Rochlis . |
| 3,390,447 | 7/1968 | Mears . |
| 3,485,705 | 12/1969 | Harmon . |
| 3,560,601 | 2/1971 | Johnson et al. . |
| 3,674,221 | 7/1972 | Riemersma . |
| 3,703,897 | 11/1972 | Mack et al. . |
| 3,814,101 | 6/1974 | Kozak . |
| 3,844,027 | 10/1974 | Hagen et al. . |
| 3,929,135 | 2/1975 | Thompson . |
| 3,945,386 | 3/1976 | Anczurowski et al. . |
| 3,952,745 | 4/1976 | Duncan . |
| 3,957,414 | 5/1976 | Bussey, Jr. et al. . |
| 3,967,623 | 7/1976 | Butterworth et al. . |

(List continued on next page.)

FOREIGN PATENT DOCUMENTS

| | | |
|---|---|---|
| 2014508 | 8/1979 | United Kingdom . |
| 2014903 | 9/1979 | United Kingdom . |

*Primary Examiner*—Mary Beth Jones
*Assistant Examiner*—P. Zuttarelli
*Attorney, Agent, or Firm*—Kevin C. Johnson; William Scott Andes; E. Kelly Linman

[57] ABSTRACT

A resilient three-dimensional plastic web exhibiting reduced skin contact area and a fiber-like appearance and tactile impression. The web has a multiplicity of apertures therein, each being defined by a multiplicity of intersecting fiber-like elements interconnected to one another in the plane of a first surface of the web. Each of the fiber-like elements exhibits a substantially uniform generally upwardly concave-shaped cross-section along its length. The cross-section comprises a pair of convergent substantially linear portions which intersect one another at an end to form a vertex in the plane of the first surface of the web. This vertex reduces the skin contact area of the web providing a more comfortable feel for the user when the web is employed as a wearer contacting topsheet on an absorbent article. Furthermore, the web provides a substantially non-glossy visible surface as there is almost no substantially planar portion in its uppermost surface to reflect incident light to the viewer's eye. The pattern of intersecting vertices in the first surface of the web substantially eliminates pooling of fluid on the first surface of the web, since there is almost no substantially planar portion on which fluid may pool. This further contributes to the web's clean and dry appearance in use as well as more rapid fluid transport into the underlying absorbent element.

20 Claims, 11 Drawing Sheets

U.S. PATENT DOCUMENTS

| | | | |
|---|---|---|---|
| 3,979,494 | 9/1976 | Ericson. | |
| 3,989,867 | 11/1976 | Sisson. | |
| 4,038,040 | 7/1977 | Nagl. | |
| 4,041,951 | 8/1977 | Sanford. | |
| 4,077,410 | 3/1978 | Butterworth et al.. | |
| 4,133,310 | 1/1979 | Lloyd et al.. | |
| 4,151,240 | 4/1979 | Lucas et al.. | |
| 4,276,338 | 6/1981 | Ludwa et al.. | |
| 4,323,069 | 4/1982 | Ahr et al. | 604/372 |
| 4,342,314 | 8/1982 | Radel et al.. | |
| 4,395,215 | 7/1983 | Bishop. | |
| 4,463,045 | 7/1984 | Ahr et al.. | |
| 4,535,020 | 8/1985 | Thomas et al.. | |
| 4,591,523 | 5/1986 | Thompson. | |
| 4,609,518 | 9/1986 | Curro et al.. | |
| 4,629,643 | 12/1986 | Curro et al.. | |
| 4,637,819 | 1/1987 | Ouellette et al.. | |
| 4,681,793 | 7/1987 | Linman et al.. | |
| 4,695,422 | 9/1987 | Curro et al.. | |
| 4,747,991 | 5/1988 | Bishop. | |
| 4,772,444 | 9/1988 | Curro et al.. | |
| 4,778,644 | 10/1988 | Curro et al.. | |
| 4,839,216 | 6/1989 | Curro et al.. | |
| 4,846,821 | 7/1989 | Lyons et al.. | |
| 4,859,519 | 8/1989 | Cabe, Jr. et al.. | |
| 5,342,334 | 8/1994 | Thompson et al. | 604/358 |
| 5,368,910 | 11/1994 | Langdon | 604/385.1 |

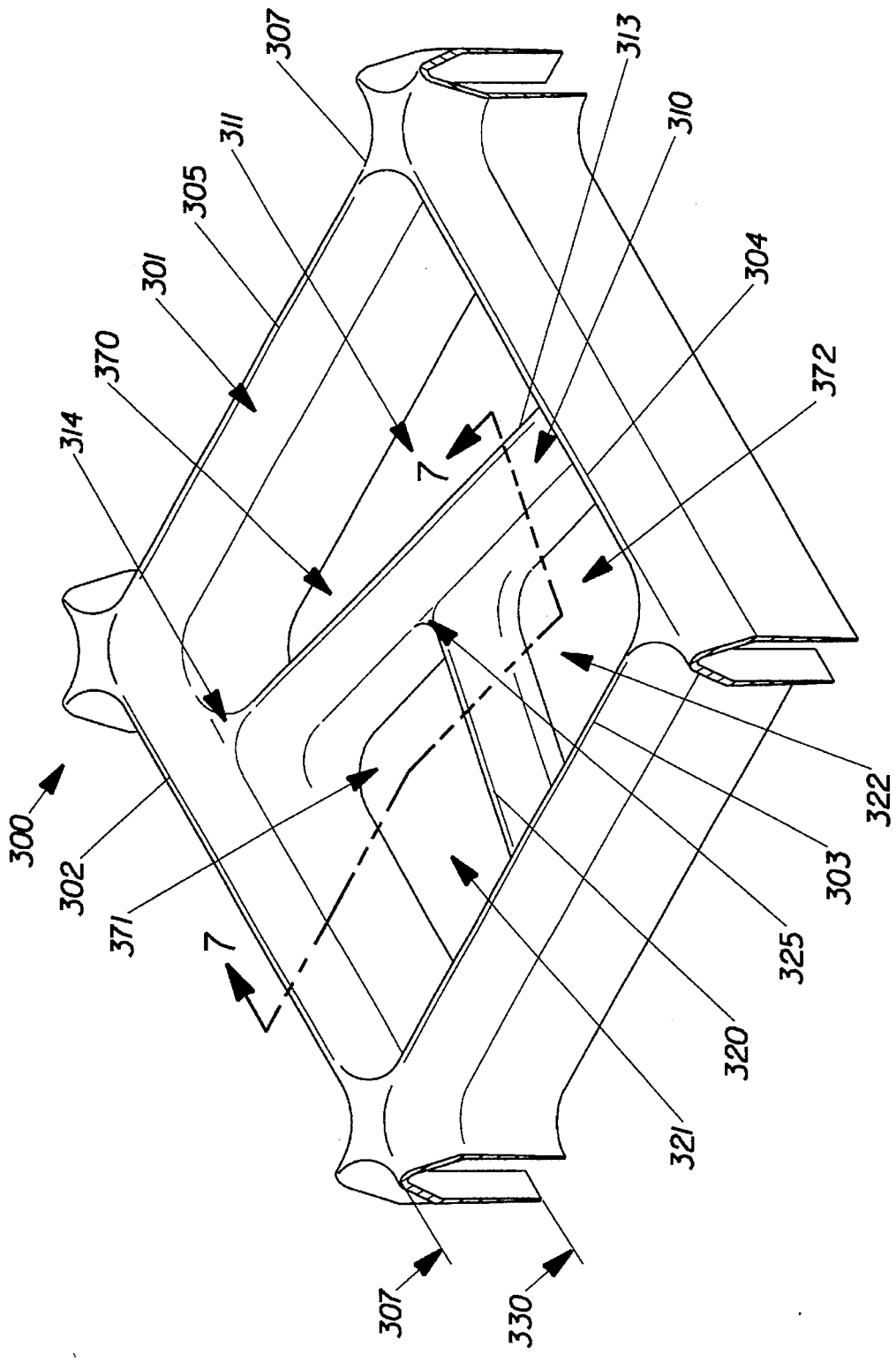

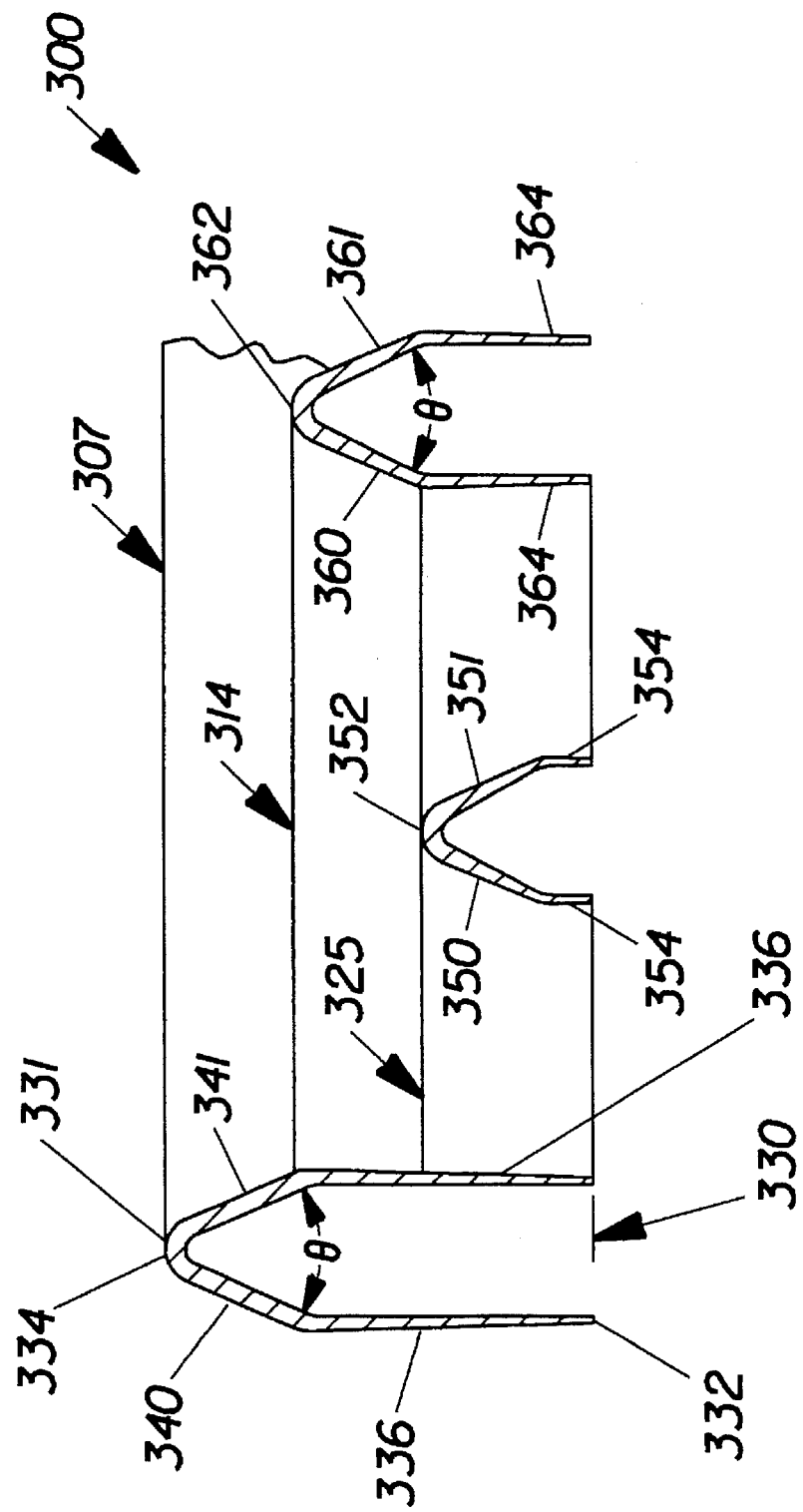

RESILIENT PLASTIC WEB EXHIBITING REDUCED SKIN CONTACT AREA AND ENHANCED FLUID TRANSFER PROPERITES

CROSS-REFERENCE TO RELATED APPLICATIONS

This application is a continuation-in-part of application Ser. No. 08/146,675, filed Nov. 1, 1993 (now abandoned), which is a continuation-in-part of application Ser. No. 07/817,016, filed Jan. 3, 1992 (now abandoned).

FIELD OF THE INVENTION

The present invention relates to resilient, three-dimensional, fluid-pervious plastic webs exhibiting reduced skin contact area, a fiber-like appearance and tactile impression, and more particularly, to such webs having enhanced fluid transfer properties.

BACKGROUND INFORMATION

It has long been known in the disposable absorbent article art that it is extremely desirable to construct absorptive devices, such as disposable diapers, sanitary napkins, incontinent articles, and the like, presenting a dry surface feel to the user to improve wearing comfort and to minimize the development of undesirable skin conditions due to prolonged exposure to moisture absorbed within the article.

One viable prior art solution to the aforementioned problem is disclosed in commonly assigned U.S. Pat. No. 4,342,314 issued to Radel et al. on Aug. 3, 1982 and hereby incorporated herein by reference. Radel et al. discloses an absorbent article with a wearer-contacting topsheet comprising a resilient, macroscopically expanded, three-dimensional plastic web exhibiting a combination of fiber-like and plastic properties. In a preferred embodiment, the macroscopically expanded, three-dimensional plastic web topsheet disclosed in Radel et al. exhibits a fine scale three-dimensional microstructure comprising a regulated continuum of capillary networks, of steadily decreasing size, originating in and extending from one surface of the web and terminating in the form of apertures in the opposite surface thereof to promote rapid fluid transport in the direction of decreasing capillary size. The web's fiber-like appearance is comprised of a continuum of fiber-like elements, the opposed ends of each of the fiber-like elements being interconnected to at least one other of the fiber-like elements.

A typical capillary network in the Radel et al. structure comprises an uppermost capillary opening formed by a multiplicity of primary fiber-like elements interconnected to one another in the uppermost plane of the web. The uppermost opening may, if desired, be further subdivided into smaller capillary openings by secondary and tertiary fiber-like elements at planes located below the wearer-contacting surface of the web.

Each of the fiber-like elements exhibits a substantially uniform U-shaped cross-section along its length. In the case of a primary fiber-like element, its cross-section comprises a base portion located in the wearer-contacting plane and a sidewall portion joined to each edge of the base portion and extending generally in the direction of the absorbent pad-contacting surface of the web. The sidewall portions which intersect one another are joined to one another intermediate the wearer contacting surface and the absorbent pad contacting surface of the web, thereby forming a capillary network interconnecting the opposed surfaces of the web. The secondary and tertiary fiber-like elements, when employed, are generally similar, but originate in planes below the wearer-contacting surface of the web.

One drawback associated with the use of topsheets comprised of plastic is that despite their superior fluid handling characteristics some users are very reluctant to place a topsheet which they readily perceive as plastic by virtue of its glossy appearance in contact with their skin.

To reduce the gloss on the web's visible surface, i.e., that portion of the web which is visible from directly overhead, it has been learned that inclusion of a microscopic pattern of surface aberrations which are not discernible when the perpendicular distance between the viewer's eye and the plane of the web is about twelve inches is highly effective. Commonly assigned U.S. Pat. No. 4,463,045 issued to Ahr et al. on Jul. 31, 1984 and hereby incorporated herein by reference defines the relevant criteria which must be satisfied so that the three-dimensionally expanded web will exhibit a substantially non-glossy visible surface.

A topsheet of the type generally disclosed in Radel et al., having surface aberrations according to Ahr et al., exhibits a fiber-like appearance and tactile impression as well as a non-glossy visible surface. In addition, it is highly effective in promoting rapid fluid transfer from the first wearer contacting surface to the second absorbent pad contacting surface of the topsheet. Topsheets of the latter type have enjoyed widespread commercial success on catamenial pads due to their clean and dry appearance in use when contrasted to conventional nonwoven fibrous topsheets.

Nonetheless, it will be readily appreciated that even further improvement in clean and dry appearance is use are highly desirable in products of this type.

Accordingly, it is an object of the present invention to provide, in a particularly preferred embodiment, a fluid pervious plastic web which retains the foregoing benefits of Radel et al. and Ahr et al., yet which exhibits an even cleaner and drier appearance in use.

It is another object of the present invention to provide, in a particularly preferred embodiment, a fluid pervious plastic web which retains the foregoing but which also exhibits enhanced fluid transfer properties in use.

It is still another object of the present invention to provide, in a particularly preferred embodiment, a fluid pervious plastic web exhibiting a fiber-like appearance and tactile impression, i.e., an overall impression of softness, said web further exhibiting a fine scale three-dimensional microstructure comprising a regulated continuum of capillary networks, preferably of steadily decreasing size originating in and extending from one surface of said film and terminating in the form of apertures in the opposite surface thereof to promote rapid fluid transport in the direction of decreasing capillary size. As utilized herein, the term "microstructure" refers to a structure of such fine scale that its precise detail is readily perceived by the human eye only upon magnification by a microscope or means well known in the art. The term "fiber-like", as utilized herein to describe the appearance of plastic webs of the present invention, refers generally to any fine scale pattern of embossments or apertures, random or nonrandom, reticulated or nonreticulated, which connotes an overall appearance and impression of a woven or nonwoven fibrous web when viewed by the human eye. When describing the elements used to form the web of the present invention, the term "fiber-like" is utilized herein to describe the appearance or shape of the elements. As utilized herein, the term "macroscopically expanded", when used to describe three-dimensional plastic webs, ribbons and films, refers to webs, ribbons and films which have been caused to conform to the surface of a three-dimensional forming structure so that both surfaces thereof exhibit the three-dimensional pattern of said forming structure, said pattern being readily visible to the naked eye when the perpendicular distance between the viewer's eye and the plane of the web is about twelve inches. Such macroscopically expanded webs, ribbons and films are typically caused to conform to the surface of said forming structures by embossing, i.e., when the forming structure exhibits a pattern comprised primarily of male projections, by debossing, i.e., when the forming structure exhibits a pattern comprised primarily of female capillary networks, or by extrusion of a resinous melt directly onto the surface of a forming structure of either type. By way of contrast, the term "planar", when utilized herein to describe plastic webs, ribbons and films, refers to the overall condition of the web, ribbon or film when viewed by the naked eye on a macroscopic scale.

SUMMARY OF THE INVENTION

The present invention pertains, in a preferred embodiment, to a resilient three-dimensional web having a first surface in a first plane and a second surface in a second plane. The web exhibits a fiber-like appearance and tactile impression. The web is comprised of a fluid-impervious plastic material. The first surface of the web has a multiplicity of apertures therein. Each of the apertures is defined by a multiplicity of intersecting fiber-like elements interconnected to one another in the first plane of the web. Each of the fiber-like elements exhibits a substantially uniform generally upwardly concave-shaped cross-section along its length. The cross-section comprises a pair of convergent substantially linear portions which intersect one another at an end to form a single vertex in the first plane. The vertex defines an angle theta ($\theta$) such that theta ($\theta$) is from about 20° to about 140°. The cross-section further comprises a sidewall portion joined to a free end of each of the linear portions. The sidewall portions extend generally in the direction of the second surface of the web. The intersecting substantially linear portions and the intersecting sidewall portions are interconnected to one another respectively intermediate the first and second surfaces of the web. The interconnected sidewall portions terminate substantially concurrently with one another in the second plane of the web.

In another preferred embodiment, the present invention provides an absorbent article comprising a wearer-contacting topsheet and an absorbent element for absorbing bodily fluids. The topsheet comprises a resilient three-dimensional web having a first surface in a first plane for contacting the wearer and a second surface in a second plane having a multiplicity of apertures therein contacting a surface of the absorbent element. The web is comprised of a fluid-impervious plastic material. The web exhibits reduced skin contact area, a fiber-like appearance and tactile impression. The first surface of the web has a multiplicity of apertures therein. Each of the apertures is defined by a multiplicity of intersecting fiber-like elements interconnected to one another in the first plane of the web. Each of the fiber-like elements exhibits a substantially uniform generally upwardly concave-shaped cross-section along its length. The cross-section comprises a pair of convergent substantially linear portions which intersect one another at an end to form a single vertex in the first plane. The vertex defines an angle theta ($\theta$) such that theta ($\theta$) is from about 20° to about 140°. The cross-section further comprises a sidewall portion joined to a free end of each of the linear portions. The sidewall portions extend generally in the direction of the second surface of the web. The intersecting substantially linear portions and the intersecting sidewall portions are interconnected to one another respectively intermediate the first and second surfaces of the web. The interconnected sidewall portions terminate substantially concurrently with one another in the second plane of the web.

BRIEF DESCRIPTION OF THE DRAWINGS

While the specification concludes with claims particularly pointing out and distinctly claiming the present invention, it is believed the present invention will be better understood from the following description in conjunction with the accompanying drawings in which:

FIG. 6 is an enlarged, partially segmented perspective illustration of an alternative fiber-like plastic web of the present invention;

FIG. 7 is an enlarged cross-sectional illustration of a web of the type generally shown in FIG. 6 taken along section line 7—7 in FIG. 6;

DETAILED DESCRIPTION OF THE PRESENT INVENTION

As used herein, the term "absorbent article" refers to devices which absorb and contain body exudates, and, more specifically, refers to devices which are placed against or in proximity to the body of the wearer to absorb and contain the various exudates discharged from the body. The term "absorbent article" is intended to include diapers, catamenial pads, sanitary napkins, pantiliners, incontinent pads and the like. The term "disposable" is used to herein to describe absorbent articles which are not intended to be laundered or otherwise restored or reused as an absorbent article (i.e., they are intended to be discarded after a single use, and, preferably to be recycled, composted or otherwise disposed of in an environmentally compatible manner). While the present invention will be described in the context of providing a fluid pervious, resilient, three-dimensional plastic web exhibiting reduced skin contact area, as well as a fiber-like appearance and tactile impression and exhibiting enhanced fluid transfer properties when employed as a topsheet on an absorbent article such as a disposable diaper or disposable catamenial appliance, the present invention is in no way limited to such application. To the contrary, the present invention may be practiced to great advantage in many situations where it is desired to produce a plastic film or web exhibiting either a perforate or an imperforate three-dimensional structure having properties, characteristics, aesthetics, fineness of detail, etc., not previously disclosed in the prior art. The patterns created may be of any desired shape, they may be regulated or random, reticulated or non-reticulated, continuous or interrupted, perforated or unperforated or any desired combination thereof. The detailed description of a preferred structure and its use as a topsheet in a disposable diaper will allow one skilled in the art to readily adapt the invention to other devices.

Figure 1:
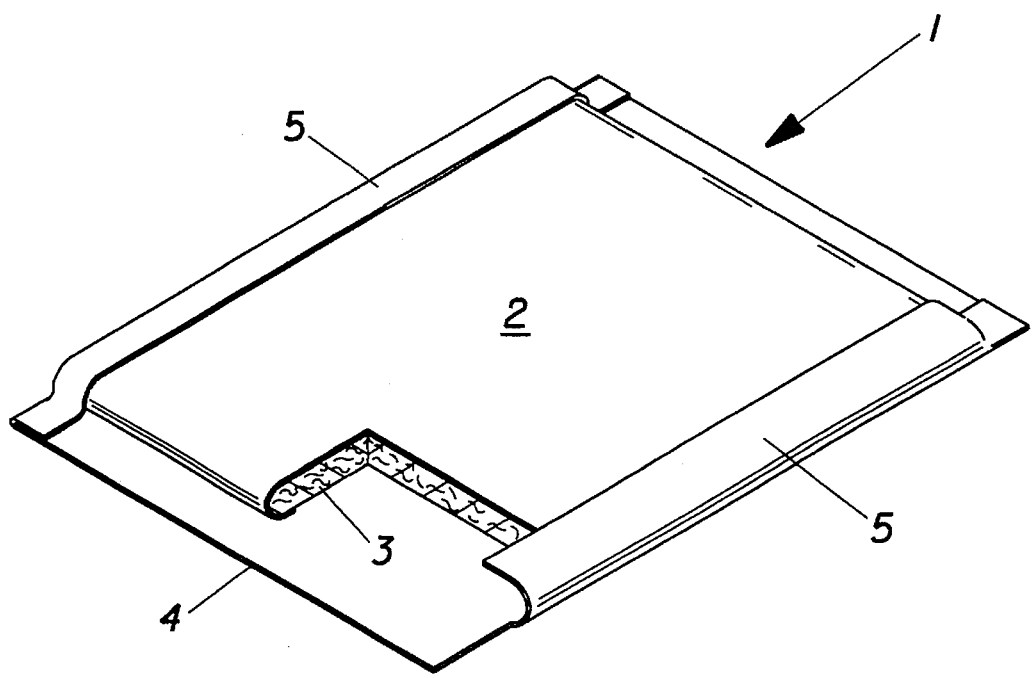
FIG. 1 is a simplified perspective representation of an unfolded absorbent article with portions of its components cut away.

FIG. 1 is a perspective view of a representative absorbent article in an unfolded condition. Various layers have been cut away to more clearly show the structural details of this embodiment. The absorbent article is referred to generally by the reference numeral 1. The fluid-pervious topsheet is shown at 2. The other two major components of the absorbent article 1 are the absorbent element or pad 3 and the fluid-impervious backsheet 4. In general, the side flaps 5 of the backsheet 4 are folded so as to cover the edges of the absorbent pad 3 and topsheet 2. Topsheet 2 is generally folded to completely enclose the ends of the absorbent pad 3. The drawing of absorbent article 1 in FIG. 1 is a simplified representation of an absorbent article. A more detailed description of a preferred embodiment of a disposable diaper generally in accordance with the absorbent article depicted in FIG. 1 is contained in U.S. Pat. No. 3,952,745 issued to Duncan on Apr. 27, 1976, said patent being hereby incorporated herein by reference.

Figure 2:
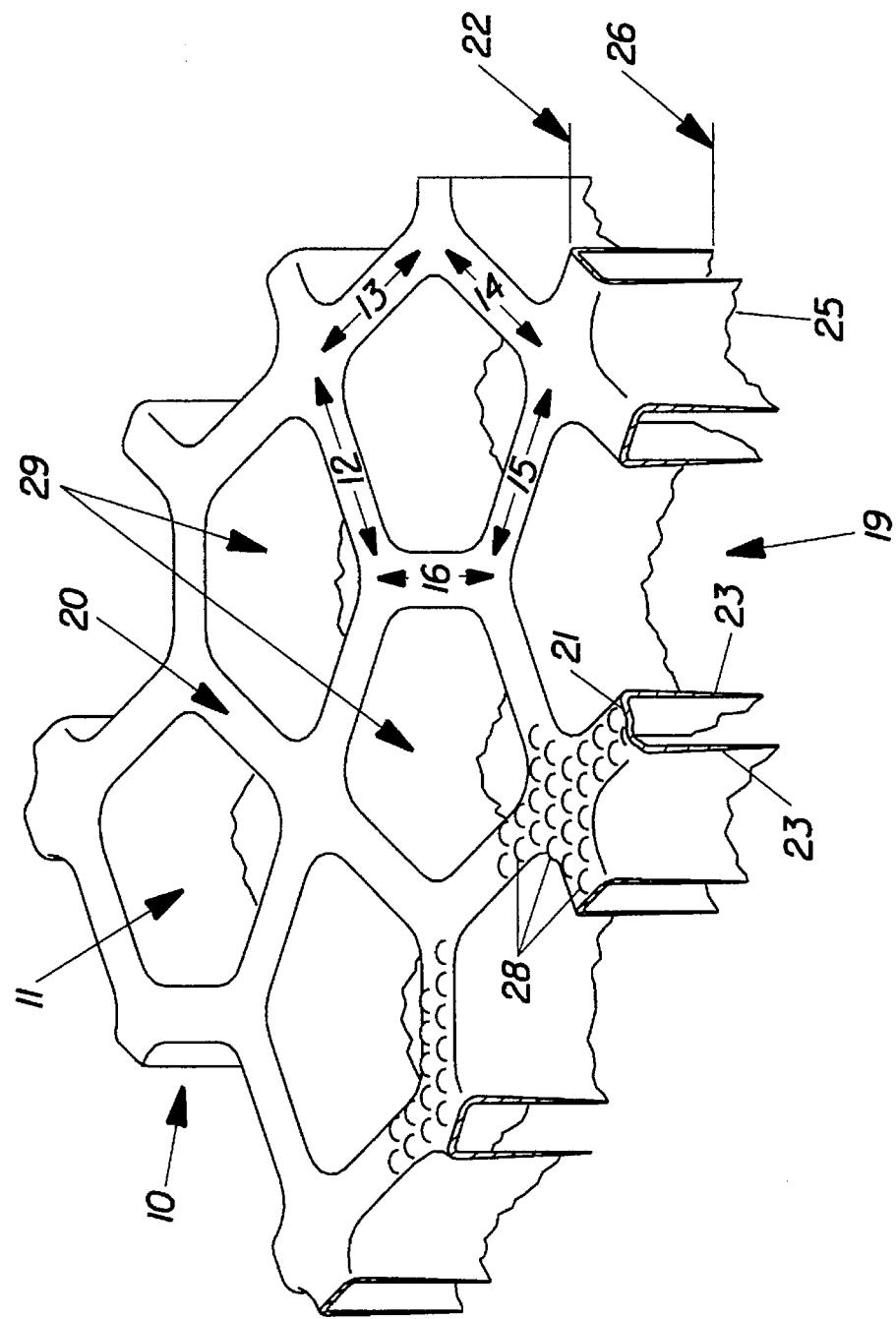
FIG. 2 is an enlarged, partially segmented, perspective illustration of a prior art plastic web of the type generally disclosed in U.S. Pat. No. 4,342,314.

FIG. 2 is an enlarged, partially segmented, perspective illustration of a prior art three-dimensional, fiber-like, fluid pervious plastic web 10 which has been found highly suitable for use as a topsheet in disposable absorbent articles, such as diapers and sanitary napkins. The prior art web 10 is generally in accordance with the teachings of commonly assigned U.S. Pat. No. 4,342,314 issued to Radel et at. on Aug. 3, 1982 and incorporated herein by reference. The fluid pervious plastic web 10 illustrated in FIG. 2 exhibits a multiplicity of apertures, e.g., apertures 11, which are formed by a multiplicity of intersecting fiber-like elements, e.g., elements 12, 13, 14, 15, and 16, interconnected to one another in the first surface 20 of the web. Each fiber-like element comprises a base portion, e.g., base portion 21, located in plane 22. Each base portion has a sidewall portion, e.g., sidewall portions 23, attached to each edge thereof. The sidewall portions extend generally in the direction of the second surface 25 of the web. The intersecting sidewall portions of the fiber-like elements are interconnected to one another intermediate the first and second surfaces of the web, and terminate substantially concurrently with one another in the plane 26 of the second surface.

In a particularly preferred embodiment, the base portion 21 includes a microscopic pattern of surface aberrations 28, generally in accordance with the teachings of commonly assigned U.S. Pat. No. 4,463,045 issued to Ahr et at. on Jul. 31, 1984 and incorporated herein by reference. The microscopic pattern of surface aberrations 28 provide a substantially non-glossy visible surface when the web is struck by incident light rays.

In a particularly preferred embodiment, the interconnected sidewall portions terminate substantially concurrently with one another in the plane of the second surface to form apertures 19 in the second surface 25 of the web. The capillary network 29 formed by the interconnected sidewall portions allows for free transfer of fluid from the first surface of the web directly to the second surface of the web without lateral transmission of the fluid between adjacent capillary networks.

Despite the effective functioning of the prior art fluid pervious web 10 in topsheet applications for disposable absorbent articles such as catamenial pads, it has been observed that on occasion fluid, particularly menses, deposited on the first surface of the fiber-like elements tends to collect or pool on the substantially planar base portions 21 of the fiber-like elements, thereby creating an uncomfortable wet feeling for the user since the retained fluid is in direct contact with the user's skin. If the fluid in question is colored, such as menses, the retained fluid also detracts from the normally clean appearance of the topsheet.

Figure 3:
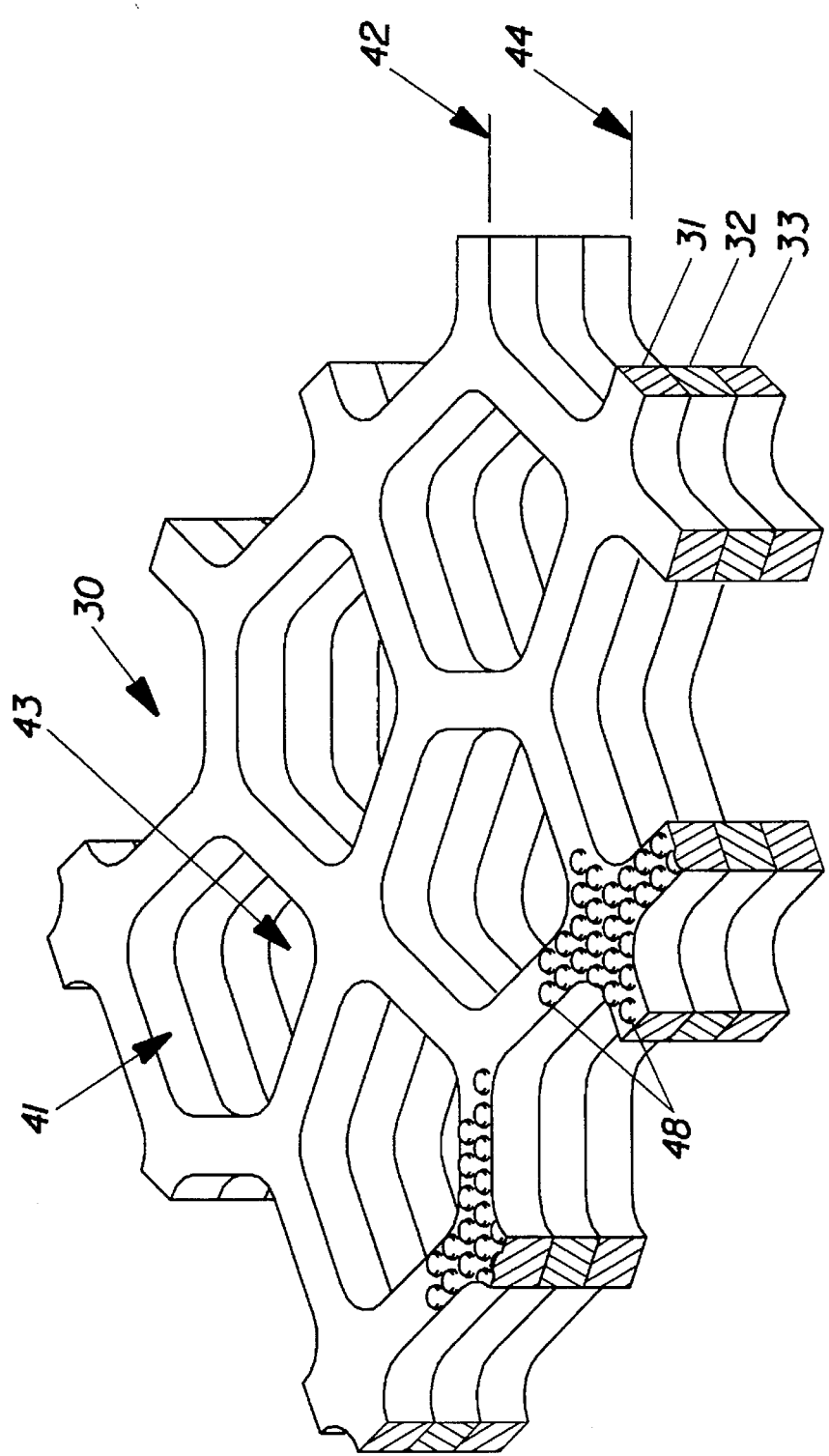
FIG. 3 is an enlarged, partially segmented, perspective illustration of a photoetched laminate structure of the type used to form plastic webs of the type generally illustrated in FIG. 2.

FIG. 3 is an enlarged perspective illustration of a photoetched laminate structure 30 which can be utilized to vacuum form an initially impervious, substantially planar, heated plastic film to produce the prior art fluid pervious fiber-like web 10 of the type generally illustrated in FIG. 2. The laminate structure 30 is preferably constructed generally in accordance with the teachings of commonly assigned U.S. Pat. No. 4,342,314 issued to Radel et at. on Aug. 3, 1982, incorporated herein by reference and is comprised of individual lamina 31, 32 and 33. The aperture patterns in each lamina are identical to one another. A comparison of FIG. 3 with the fiber-like plastic web 10 shown in FIG. 2 reveals the correspondence of capillary opening 11 in the uppermost plane 22 of the plastic web 10 to opening 41 in the uppermost plane 42 of the photoetched laminate structure 30. Likewise, capillary opening 19 in lowermost plane 26 of plastic web 10 corresponds to opening 43 in lowermost plane 44 of photoetched laminate structure 30.

The uppermost surface of photoetched laminate structure 30 located in uppermost plane 42 is provided with a microscopic pattern of protuberances 48. This is preferably accomplished by applying a resist coating which corresponds to the desired microscopic pattern of surface aberrations to the top side of a planar photoetched lamina 31, and thereafter initiating a second photoetching process. The second photoetching process produces a lamina 31 having a microscopic pattern of protuberances 48 on the uppermost surface of the interconnected fiber-like elements defining the pentagonally shaped apertures, e.g., aperture 41. Construction of a laminate structure employing such a pattern of protuberance 48 on its uppermost layer is generally disclosed in commonly assigned U.S. Pat. No. 4,463,045 issued to Ahr et al. on Jul. 31, 1984 and incorporated herein by reference.

Figure 4:
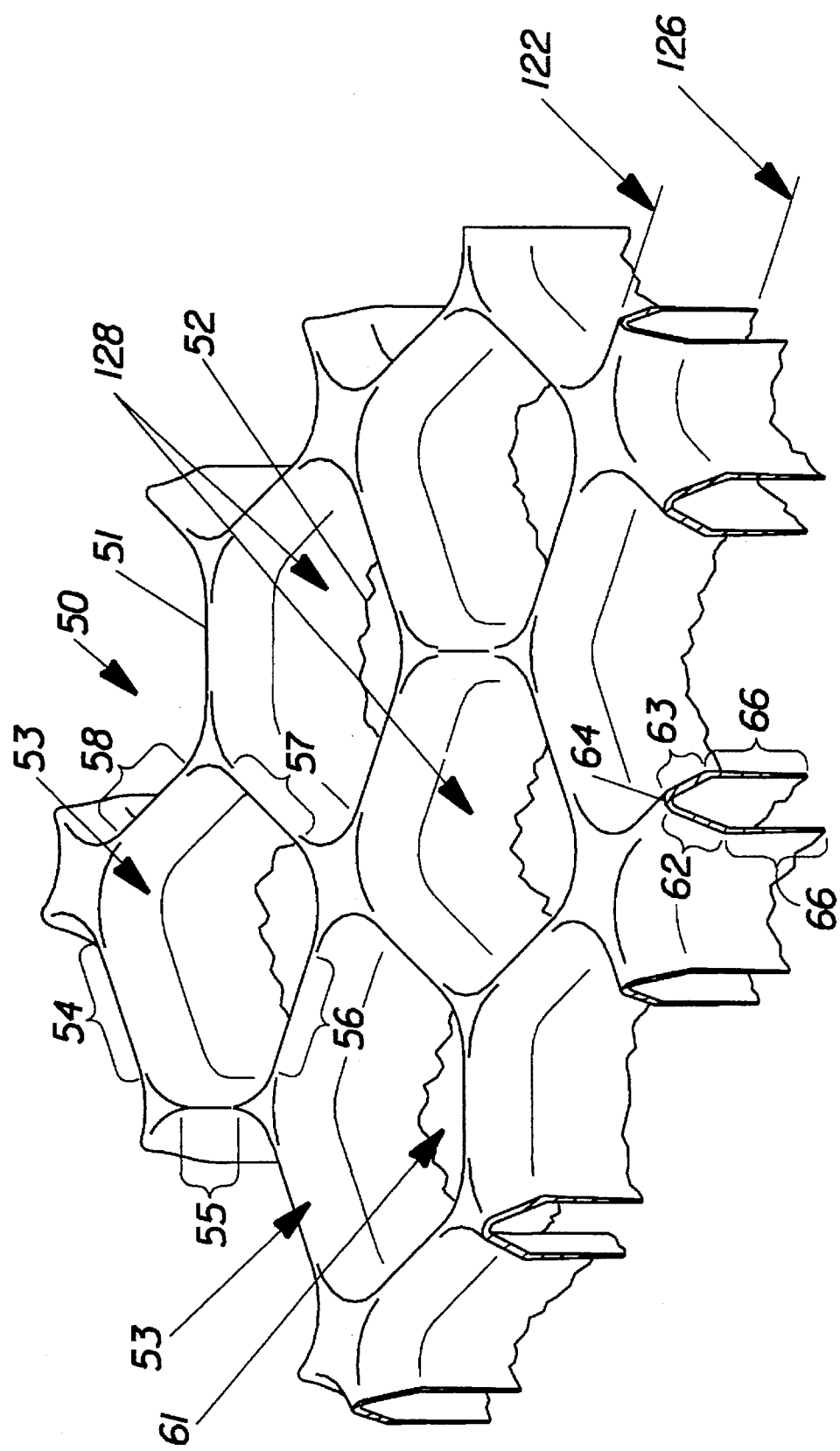
FIG. 4 is an enlarged, partially segmented perspective illustration of a preferred fiber-like plastic web of the present invention.

FIG. 4 is an enlarged, partially segmented, perspective illustration of a preferred embodiment of a three-dimensional, fiber-like, fluid pervious plastic web 50 of the present invention. As can be seen in FIG. 4 the web's fiber-like appearance is comprised of a continuum of fiber-like elements, the opposed ends of each of said fiber-like elements being interconnected to at least one other of said fiber-like elements. In the embodiment disclosed in FIG. 4, the interconnected fiber-like elements form a pattern of pentagonally shaped capillary networks 128. The fiber-like plastic web 50 is particularly well suited for use as a topsheet on an absorbent article, such as a diaper or catamenial pad. The web 50, which exhibits a fiber-like appearance, embodies a three-dimensional microstructure comprising a regulated continuum of capillary networks 128 of steadily decreasing size extending from the web's uppermost or wearer-contacting surface 51 in plane 122 to its lowermost or absorbent pad-contacting surface 52 in plane 126 to promote rapid fluid transport from the uppermost surface 51 to the lowermost surface 52 of the web without lateral transmission of said fluid between adjacent capillary networks 128.

Apertures 53 are formed by a multiplicity of intersecting fiber-like elements, e.g., elements 54, 55, 56, 57, and 58, interconnected to one another in the first surface 51 of the web. As shown in partial cross-section in FIG. 4, each fiber-like element comprises a pair of convergent substantially linear portions, e.g., linear portions 62 and 63, which intersect one another at an end to form a single vertex 64 in the first plane 122. Each substantially linear portion has a sidewall portion, e.g., sidewall portions 66, joined to a free end of the substantially linear portions. The sidewall portions 66 extend generally in the direction of the second surface 52 of the web. The intersecting substantially linear portions and the intersecting sidewall portions are interconnected to one another, respectively, intermediate the first and second surfaces of the web. The interconnected sidewall portions 66 terminate substantially concurrently with one another in the second plane of the web. In a particularly preferred embodiment, interconnected sidewall portions terminate substantially concurrently with one another in the second plane to form apertures in the second surface of the web. The convergent substantially linear portions together with the sidewall portions produce apertures 61 in the second surface which are smaller than apertures 60 in the first surface of the web. Therefore, the capillary networks formed by the interconnected substantially linear portions and the sidewall portions are of decreasing cross-section in the direction of the second surface of the web. This decreasing cross-section aids in transporting fluid deposited on the first surface of the web directly to the second surface of the web without lateral transmission of the fluid between adjacent capillary networks.

Figure 5B:
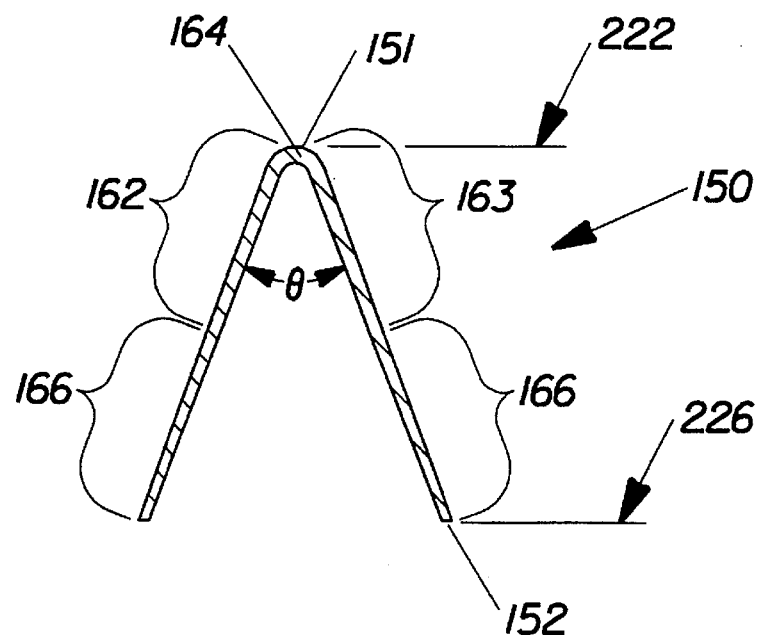
FIG. 5B is an enlarged, cross-sectional illustration of another embodiment of a fiber-like element of the plastic web of the present invention.
Figure 5A:
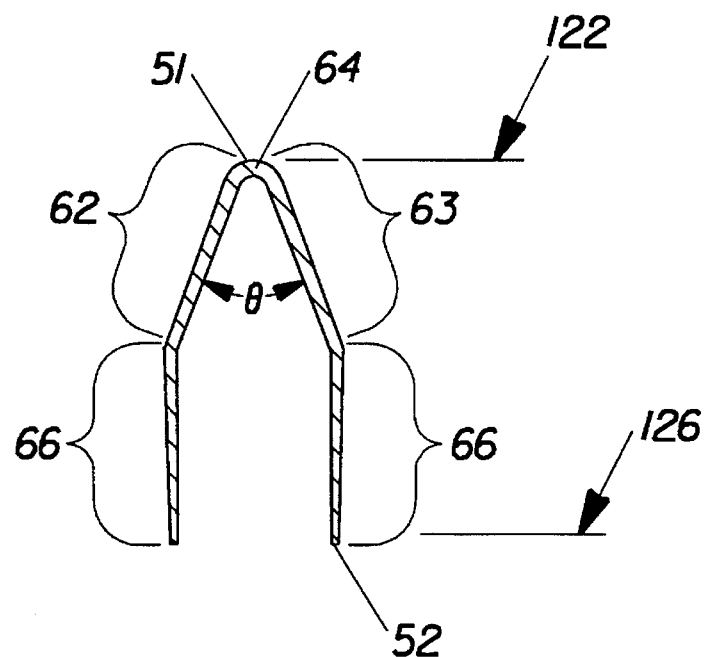
FIG. 5A is an enlarged, cross-sectional illustration of a fiber-like element of the plastic web illustrated in FIG. 4.

FIG. 5A is an enlarged cross-sectional illustration of a fiber-like element of the plastic web of FIG. 4. The fiber-like element exhibits a substantially uniform generally upwardly concave-shaped cross-section which extends along the length of the fiber-like element. In this embodiment, the vertex 64 defines an angle theta (θ), between substantially linear portions 62 and 63. Preferably, angle theta (θ) is from about 20° to about 140°, more preferably from about 40° to about 120°, and most preferably from about 60° to about 100°.

When the fiber-like element of FIG. 5A is viewed from a perspective such as that of FIG. 4, substantially linear portions 62 and 63 in fact represent cross-sections through substantially planar surfaces of the fiber-like element. Accordingly, vertex 64 as shown in FIG. 5A is in reality a cross-section through a line of intersection of such substantially planar surfaces which extends along the length of the element to the vicinity of its juncture with adjoining elements. In geometrical terms, the figure formed by the intersection along vertex 64 of the substantially planar surfaces represented by substantially linear portions 62 and 63, i.e., the shape of the upper portion of the fiber-like element, may be described as a "dihedral angle". Vertex 64 preferably closely approximates a sharp line or corner of intersection of the substantially planar surfaces, although in reality vertex 64 may exhibit a very small but finite radius of curvature.

In the preferred configuration depicted in FIG. 4, the fiber-like elements are substantially linear as they span the distance between consecutive element intersections. As such, linear characteristics preferably predominate along the length of the element, although some degree of curvature is not inconsistent with the present invention. Accordingly, the substantially planar surfaces represented in cross section by substantially linear portions 62 and 63 are such that planar characteristics preferably predominate, although some degree of curvature is not inconsistent with the present invention.

FIG. 5B is a cross-sectional illustration of an alternative fiber-like element of the plastic web of the present invention. In this embodiment interconnected sidewall portions of the fiber-like elements, e.g., elements 166, are joined to the free end of the interconnected substantially linear portions, e.g. linear portions 162 and 163, at substantially the same angle with respect to said first and second surfaces. Substantially linear portions 162 and 163 intersect one another to form a single vertex 164 in the first plane 122 of the web. The apertures produced in a web of this configuration are of a generally decreasing cross-section in the direction of the second surface of the web to aid in transporting fluid deposited on the first surface 151 of the web directly to the second surface 152 of the web without lateral transmission of the fluid between adjacent capillary networks.

In the embodiment of FIG. 5B, the vertex 164 defines an angle them (θ) between substantially linear portions 162 and 163. The fiber-like element exhibits a substantially uniform generally upwardly concave-shaped cross-section which extends along the length of the fiber-like element. The angle them (θ) is preferably from about 20° to about 140°, more preferably from about 40° to about 120°, and most preferably from about 60° to about 100°.

As discussed above with respect to FIG. 5A, when the fiber-like element of FIG. 5B is viewed from a perspective such as that of FIG. 4, substantially linear portions 162 and 163 in fact represent cross-sections through substantially planar surfaces of the fiber-like element. Accordingly, vertex 164 as shown in FIG. 5B is likewise in reality a cross-section through a line of intersection of such substantially planar surfaces which extends along the length of the element to the vicinity of its juncture with adjoining elements. In geometrical terms, the figure formed by the intersection along vertex 164 of the substantially planar surfaces represented by substantially linear portions 162 and 163, i.e., the shape of the upper portion of the fiber-like element, may also be described as a "dihedral angle". Vertex 164 preferably closely approximates a sharp line or corner of intersection of the substantially planar surfaces, although in reality vertex 164 may exhibit a very small but finite radius of curvature.

As can be observed from an examination of the web embodiments disclosed in FIGS. 4 through 6, several themes remain constant. First, the apertures formed in the second surface of the web are smaller than the apertures formed in the first surface of the web. Second, the substantially planar base portion of the fiber-like elements disclosed in the prior art web of Radel et al., shown in FIG. 2 has been replaced by a pair of convergent substantially planar surfaces which intersect one another to form a dihedral angle with a single vertex in the first plane.

Both of the foregoing modifications aid in the transport of fluid deposited on the first surface of the web directly to the second surface of the web. The vertex formed by the intersection of the convergent substantially linear portions of the fiber-like elements employed in webs of the present invention is reduced to such a small dimension that it substantially prevents the pooling of fluid deposited on the first surface of the web. By replacing the substantially planar base portion 21 of the prior art web shown in FIG. 3 with substantially linear portions that form a vertex in the first surface of the web, fluid deposited on the web is unable to pool. It is therefore immediately transmitted directly to the second surface of the web and ultimately to the underlying absorbent core. The substantial elimination of fluid pooling on the web's first surface enhances both the clean and dry characteristics of the topsheet. In addition, the decreasing cross-section of the capillary networks in the directions of the web's second surface also helps to rapidly draw the fluid in the direction of the web's second surface, i.e., toward the underlying absorbent core, so the surface of an absorbent article employing a topsheet of the present invention will remain clean and dry even during periods of heavy fluid flow.

Quite unexpectedly it has also been learned that replacing the planar base portions 21 of the fiber-like elements of the prior art web shown in FIG. 3 with a pair of substantially linear portions which intersect one another to form a single vertex in the first plane of the web substantially reduces the glossy appearance of the web's visible surface, even when the microscopic pattern of surface aberrations 28 shown in FIG. 3 is not present. While not wishing to be bound, it is believed that this is due to the minimal amount of planar surface area that is actually present in the first surface of the web, i.e., the intersecting vertices of the fiber-like elements, in comparison with the substantially planar base portions of the fiber-like elements throughout the upper surface of the prior art web of Radel et al.

While the web embodiment generally disclosed in FIG. 4 represents a particularly preferred embodiment of the present invention employing only primary fiber-like elements, any number of fiber-like elements may be employed within web structures of the present invention, e.g., secondary, tertiary, etc. An example of such a structure is shown in FIG. 6. The capillary network shown in FIG. 6 comprises an uppermost capillary opening 301 formed by a multiplicity of primary fiber-like elements, e.g., elements 302, 303, 304 and 305 interconnected to one another in uppermost plane 307 of the web 300, said opening being further subdivided into smaller capillary openings 310 and 311 by secondary fiber-like element 313 at an intermediate plane 314. Capillary opening 310 is further subdivided by tertiary fiber-like element 320 into even smaller capillary openings 321 and 322, respectively, at a still lower plane 325 within web 300.

As can be seen from FIG. 7, which is taken along section line 7—7 of FIG. 7, planes 314 and 325 are generally parallel to and located intermediate uppermost plane 307 and lowermost plane 330. The resilient three-dimensional web 300 shown in FIG. 7 has a first wearer-contacting surface 331 located in uppermost plane 307 and a second pad-contacting surface 332 located in lowermost plane 330. As pointed out earlier herein, a typical capillary opening or aperture 301 located in uppermost plane 307 is defined by a multiplicity of intersecting primary fiber-like elements, e.g., elements 302, 303, 304 and 305, interconnected to one another in uppermost plane 307. Each of the primary fiber-like elements, e.g., elements 302, 303, 304 and 305, exhibits a substantially uniform generally upwardly concave-shaped cross-section along its length. Its cross-section comprises a pair of convergent primary substantially linear portions, e.g., primary linear portions 340 and 341, which intersect one another at an end to form a single vertex 334, in uppermost plane 307, and a primary sidewall portion, e.g., primary sidewall portion 336, joined to a free end of the primary substantially linear portions and extending generally in the direction of the absorbent pad-contacting surface 332 located in plane 330.

As can be seen from FIGS. 6 and 7, the intersecting primary substantially linear portions and the intersecting primary sidewall portions are interconnected to one another intermediate the first surface 331 and the second surface 332 of the web 300. The primary substantially linear portions and the primary sidewall portions are further connected to intersecting secondary fiber-like elements, e.g., secondary element 313, which also exhibits a substantially uniform generally upwardly concave-shaped cross-section along its length. The cross-section of each secondary element comprises a one pair of secondary substantially linear portions, e.g., secondary linear portions 360 and 361 which intersect one another at an end to form a secondary vertex 362, located in plane 314 intermediate the first surface 331 and the second surface 332 of the web 330. Each of the secondary substantially linear portions has a secondary sidewall portion, e.g., secondary sidewall portion 364, joined to the free end thereof. The secondary sidewall portions also extend generally in the direction of the second surface 332 of the web located in plane 330.

As is also apparent in FIGS. 6 and 7, the secondary substantially linear portions and the secondary sidewall portions are interconnected to primary fiber-like elements 302 and 304 intermediate plane 314 and the second surface 332 of web 300 located in plane 330.

In the web embodiment illustrated in FIGS. 6 and 7, the primary and secondary fiber-like elements are further connected to intersecting tertiary fiber-like elements, e.g., tertiary fiber-like elements 320, which also exhibit a generally upwardly concave-shaped cross-section along their length. The cross-section of the tertiary elements comprises a pair of tertiary substantially linear portions, e.g., linear portions 350 and 351, which intersect one another at an end to form a single tertiary vertex 352, located in plane 325. Plane 325 is located between plane 314 and the second surface 332 of the web 300. Each of the tertiary substantially linear portions has a tertiary sidewall portion, e.g., tertiary sidewall portions 354, joined to its free end. The tertiary sidewall portions also extend generally in the direction of the second surface 332 of the web 300. As is also apparent in FIGS. 6 and 7, the tertiary substantially linear portions and the tertiary sidewall portions are interconnected to primary and secondary fiber-like elements 303 and 313, respectively, between plane 325 and the second surface 332 of web.

As can clearly be seen in FIGS. 6 and 7, the intersecting primary, secondary and tertiary fiber-like elements terminate substantially concurrently with one another in the plane 330 of the second surface 332 to form a multiplicity of openings or apertures in the web's second surface, e.g., apertures 370, 371 and 372. As can also been seen in FIG. 7, the vertex of the primary, secondary and tertiary fiber-like elements, defines an angle theta ($\theta$), between the substantially linear portions of the respective fiber-like elements. Preferably, the angle theta ($\theta$) for the primary, secondary and tertiary fiber-like elements is from about 20° to about 140°, more preferably from about 40° to about 120°, and most preferably from about 60° to about 100°.

As discussed above with respect to FIGS. 5A and 5B, the intersections along vertices 334, 362, and 352, of substantially planar surfaces represented by substantially linear portions 340 and 341, 360 and 361, and 350 and 351, respectively, i.e., the shape of the upper portions of the fiber-like element, may also be described geometrically as "dihedral angles". Vertices 334, 362, and 352 preferably closely approximates a sharp line or corner of intersection of the respective substantially planar surfaces, although in reality vertices 334, 362, and 352 may exhibit a very small but finite radius of curvature.

Referring to FIGS. 6 and 7, it is clear that the interconnected primary, secondary and tertiary fiber-like elements located between the first and second surfaces of the web 300 form a discrete capillary network connecting each of the apertures, e.g., aperture 301 in the first surface 331 of the web, with a multiplicity of apertures, e.g., apertures 370, 371 and 372, in the second surface 332 of the web. As will be appreciated, the capillary networks are of nonuniform cross-section along their length, i.e., intermediate planes 307 and 330, due to: (a) the presence of the secondary and tertiary fiber-like elements; and (b) to the upwardly concave-shaped cross-section of at least the uppermost portion of all the fiber-like elements. Because the capillary networks connecting each aperture in the first surface 331 of the web exclusively with a multiplicity of apertures in the second surface 332 of the web are of decreasing cross-section in the direction of the second surface, fluid deposited on the uppermost surface 331 of the web is rapidly transmitted from a single aperture, e.g., aperture 301, in the uppermost surface of the web to a multiplicity of apertures, e.g., apertures 370, 371 and 372, in the second surface of the web without lateral transmission of the fluid between adjacent capillary networks.

As will be appreciated, the substantially uniform generally upwardly concave-shaped fiber-like elements utilized in webs of the present invention may be substantially straight along their entire length. Alternatively, they may be curvilinear, they may comprise two or more substantially straight segments or they may be otherwise oriented in any desired direction along any portion of their length. There is no requirement that the fiber-like elements be identical to one another. Furthermore, the aforementioned shapes may be combined in any desired fashion to produce whatever fiber-like pattern is desired. Regardless of the shape ultimately selected, the substantially uniform generally upwardly concave-shaped cross-section which exists along the respective lengths of the interconnected fiber-like elements helps impart resilience to fiber-like plastic webs of the present invention.

As should be readily apparent from the foregoing, the present invention, in a particularly preferred embodiment, maintains the desirable fiber-like appearance and tactile impression provided by the prior art plastic web 10 shown in FIG. 2, but at the same time decreases the amount of material that directly contacts the wearer's skin in use. In addition, the pattern of intersecting vertices on the fiber-like elements improves the transport of fluid from the wearer contacting surface to the pad contacting surface of the web, since the planar surfaces present in the uppermost surface of the web have all but been eliminated. This reduction of planar area in the uppermost surface of the web also reduces the amount of gloss exhibited by the web's visible surface when the visible surface is struck by incident light rays. Thus, the need to include a microscopic pattern of surface aberrations on the web's visible surface is less critical for webs of the present invention than for prior art webs employing substantially planar base portions.

Figure 8:
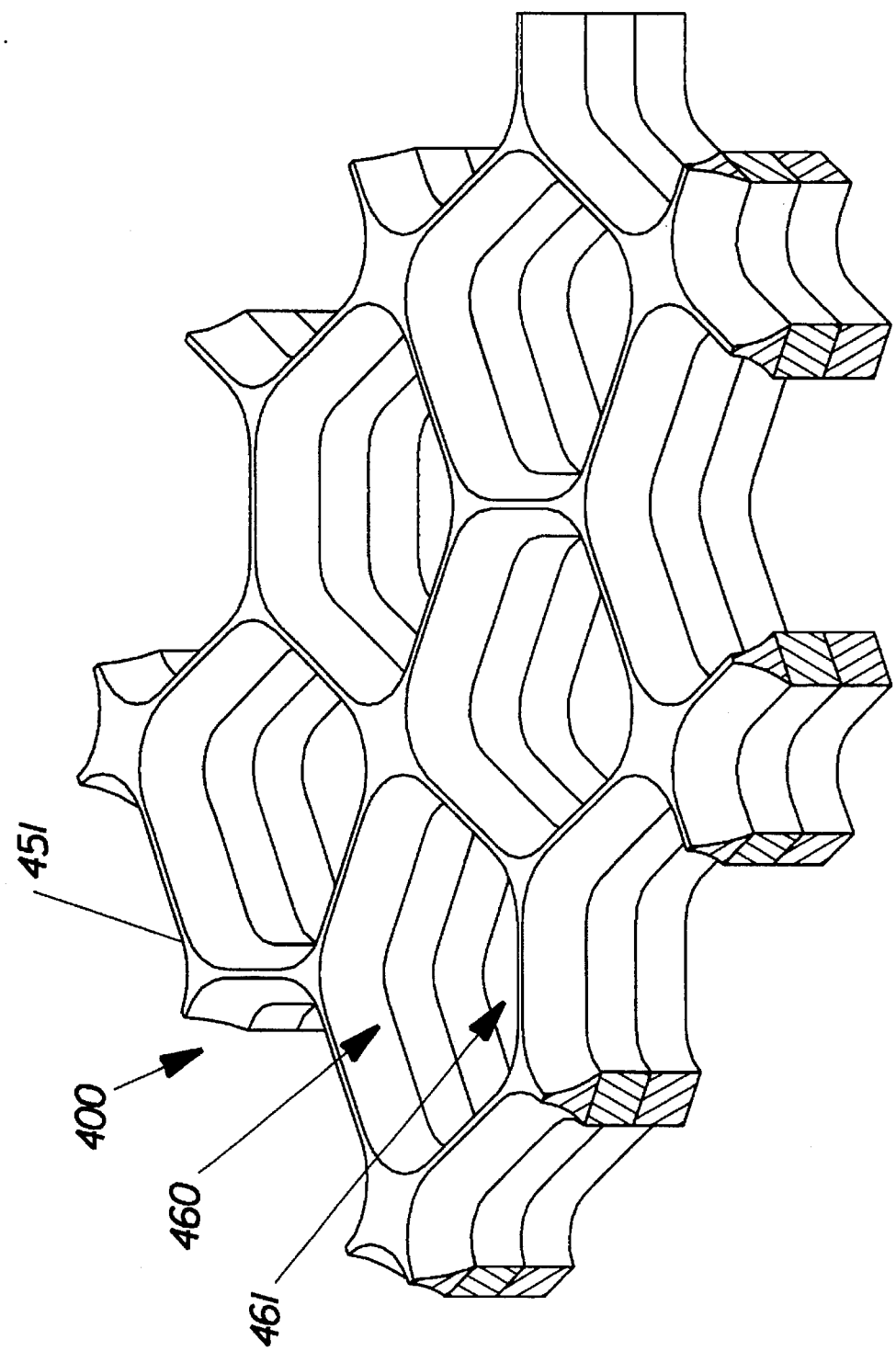
FIG. 8 is an enlarged, partially segmented perspective illustration of a photoetched laminate structure of the type used to form plastic webs of the type generally illustrated in FIG. 4.

FIG. 8 is an enlarged, partially segmented perspective illustration of a photoetched laminate structure 400 utilized to vacuum form an initially impervious, substantially planar, heated plastic film to produce a fluid pervious fiber-like web 50 of the type generally illustrated in FIG. 4. A comparison of FIG. 8 with the fiber-like plastic web 50 shown in FIG. 4 reveals the correspondence of capillary opening 53 in the uppermost plane 51 of plastic web 50 to opening 460 in the uppermost plane 451 of the photoetched laminate structure. Likewise, capillary opening 61 in the lowermost plane of plastic web 50 corresponds to the lowermost opening 461 in the lowermost plane of the photoetched laminate structure.

Figure 9:
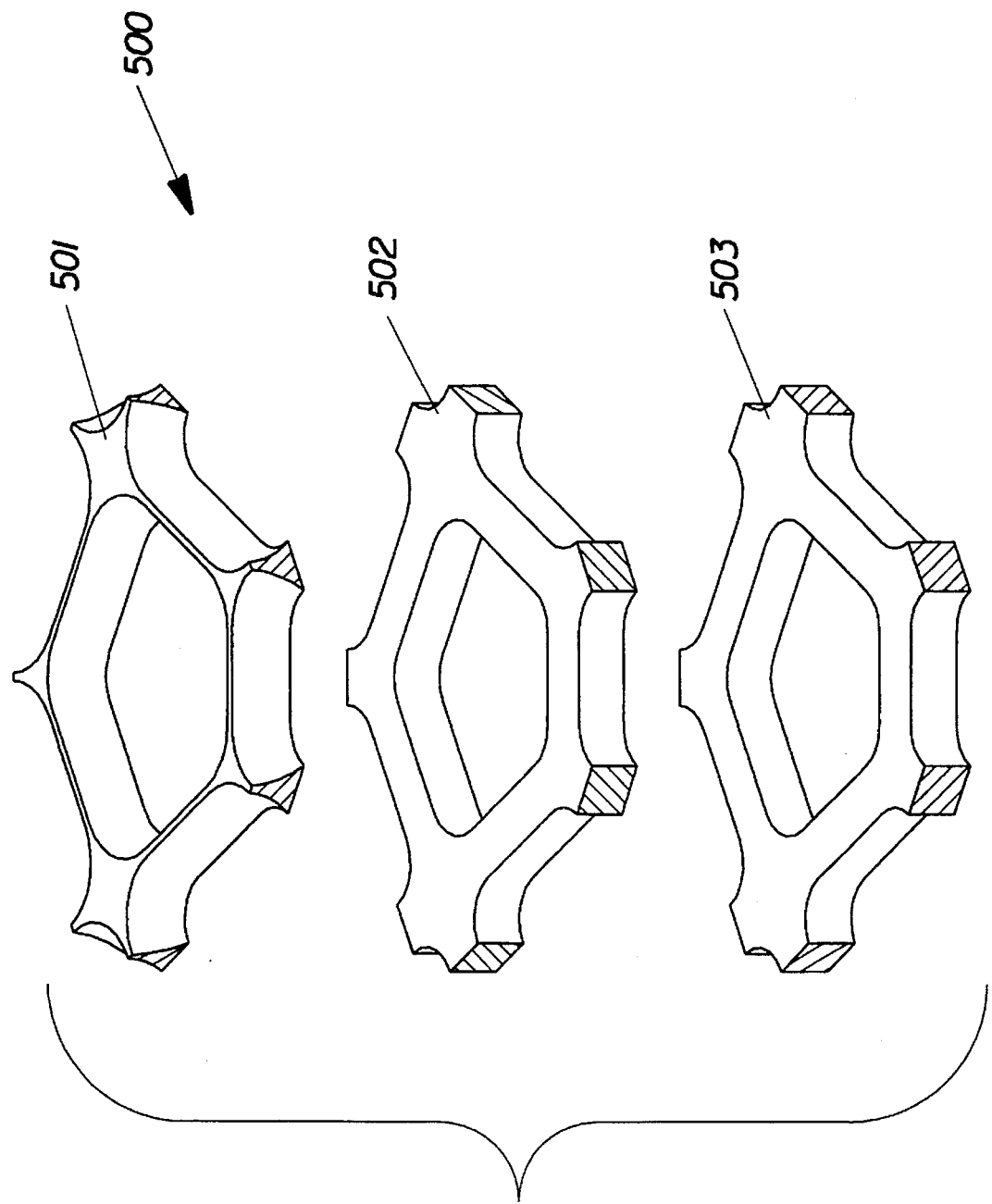
FIG. 9 is a simplified, partially exploded perspective illustration of a laminate structure similar to that illustrated in FIG. 8.

FIG. 9 is a simplified, exploded, perspective illustration of a laminate structure 500 generally similar to that of FIG. 8. The laminate structure 500 is comprised of a stack of individual lamina 501, 502 and 503. Each lamina has a pattern of openings therein. Lamina 501, 502 and 503 have the identical pattern. In practice it is typical to employ several lamina having the identical pattern superposed upon one another to provide sufficient depth of pattern to the plastic web. However, lamina 501, the uppermost lamina, has a photoetched pattern to provide a vertex in the uppermost plane. The preferred method of achieving the cross-sectional profile of lamina 501 is by chemically etching the pattern primarily from one surface. For uppermost lamina 501 the percentage of etching from the uppermost surface is usually about ninety percent (90%), although the range can be from about sixty-five to about ninety-five percent (65–95%). By way of contrast, lamina 502 and 503 are etched equally from both surfaces. A comparison of FIG. 8 with the fiber-like plastic web 50 shown in FIG. 4 reveals the correspondence of the vertex 64 in the uppermost plane 52 of plastic web 50 to the vertex 500 in the uppermost plane of the photoetched lamina 501.

Figure 10:
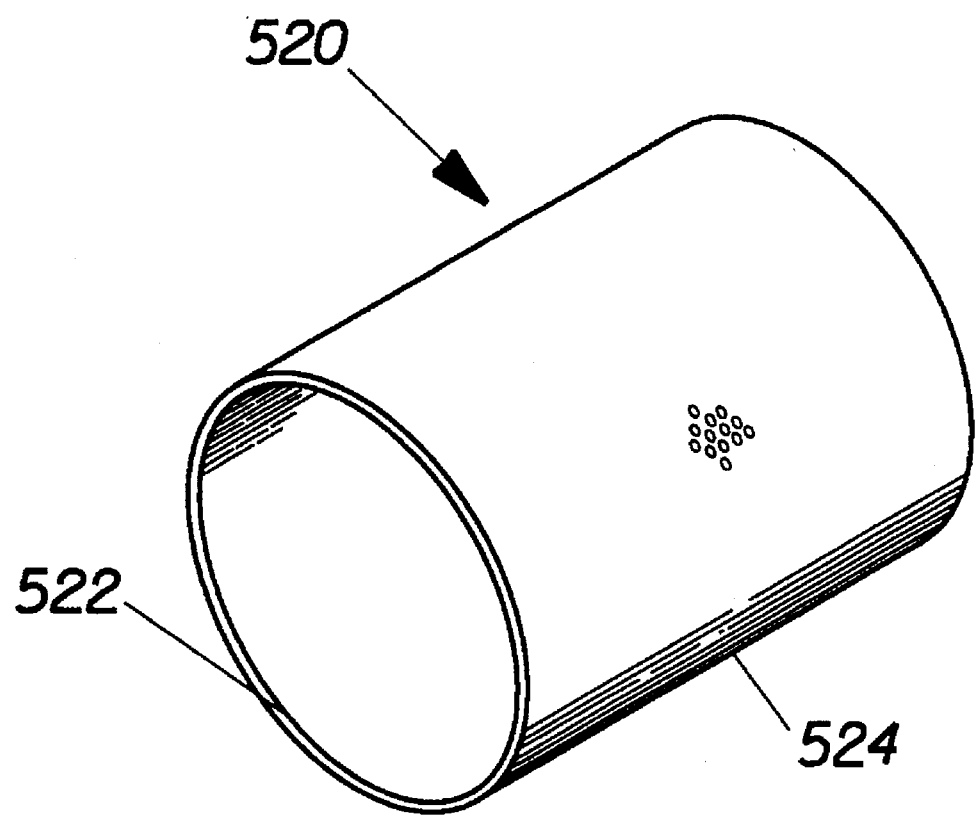
FIG. 10 is a perspective view of a tubular member formed by rolling a planar laminate structure of the type generally illustrated in FIG. 9 to the desired radius of curvature and joining the free ends thereof to one another.

Processes for constructing laminate structures of the type generally disclosed in FIG. 3 are disclosed in U.S. Pat. No. 4,342,314 issued to Radel et al. on Aug. 3, 1982, said patent being hereby incorporated herein by reference. The teachings of Radel et al. are modified to produce an uppermost lamina including a vertex, as generally described in the preceding paragraphs to produce structures of the type disclosed in FIGS. 8 and 9. The photoetched laminate structures are then preferably rolled by conventional techniques into a tubular forming member 520, as illustrated generally in FIG. 10 and their opposing ends joined generally in accordance with the teachings of Radel et al. to produce a seamless tubular forming member 520, as generally shown in FIG. 10.

Figure 11:
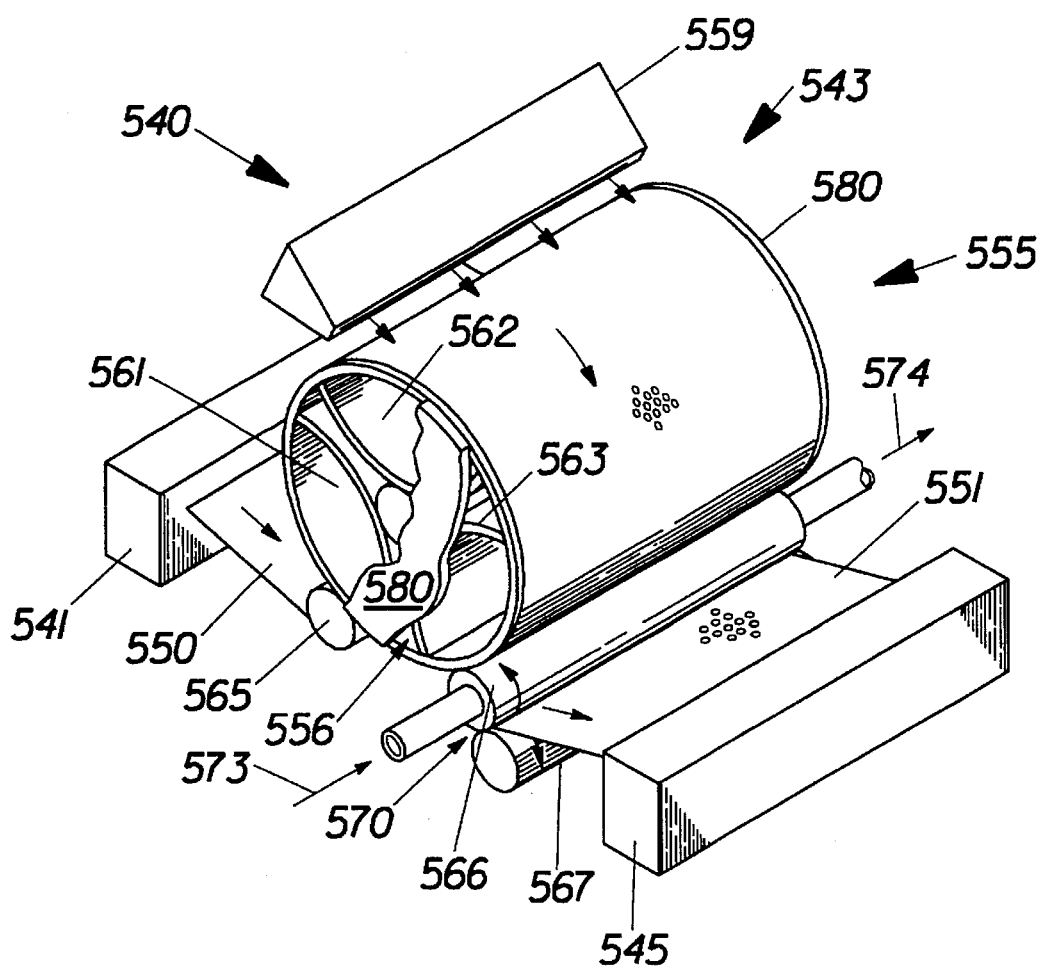
FIG. 11 is a simplified schematic illustration of a preferred method and apparatus for debossing and/or perforating a plastic film generally in accordance with the present invention.

The outermost surface 524 of the tubular forming member 520 is utilized to form the plastic web brought in contact therewith while the innermost surface 522 of the tubular member generally does not contact the plastic web during the forming operation. The tubular member may, in a preferred embodiment of the present invention, be employed as the forming surface on debossing/perforating cylinder 555 in a process of the type generally illustrated in FIG. 11 and described in detail in commonly assigned U.S. Pat. No. 4,151,240 issued to Lucas et al. on Apr. 24, 1979, said patent being incorporated herein by reference. A particularly preferred apparatus 540 of the type disclosed in said patent is schematically shown in FIG. 11. It includes constant tension film supply means 541, debossing and perforating means 543, and constant tension film forwarding and winding means 545. The frame, bearing, supports and the like which must necessarily be provided with respect to the functional members of apparatus 540 are not shown or described in detail in order to simplify and more clearly depict and disclose the present invention, it being understood that such details would be obvious to persons of ordinary skill in the art of designing plastic film convening machinery.

Briefly, apparatus 540, schematically shown in FIG. 11, comprises means for continuously convening a ribbon of thermoplastic film 550 into a debossed and perforated film 551 by directing hot air jets against one surface of the film while applying vacuum adjacent the opposite surface of the film, and while maintaining sufficient control of the film 550 to substantially obviate wrinkling and/or macroscopically distending the film. Thus, as will be more fully described hereinafter, apparatus 540 comprises means for maintaining constant machine direction tension in the film both upstream and downstream of a zone where the temperature is greater than the thermoplastic temperature of the film, but in which zone there is substantially zero machine direction and cross-machine direction tension tending to macroscopically distend the film. The tension is required to control and smooth a running ribbon of thermoplastic film; the zero tension zone results from the film in the zone being at a sufficiently high temperature to enable debossing and perforating the film through the use of heat and vacuum.

As can be seen in FIG. 11, the debossing and perforating means 543 includes a rotatably mounted debossing perforating cylinder 555 having closed ends 580, a nonrotating triplex vacuum manifold assembly 556 and hot air jet means 559. The triplex vacuum manifold assembly 556 comprises three manifolds designated 561, 562, and 563. Also shown in FIG. 11 is a freely rotatable lead-on idler roll 565, a power rotated lead-off/chill roll 566 and a soft-face (e.g., low density neoprene) roll 567 which is driven with the chill roll. Briefly, by providing means (not shown) for independently controlling the degree of vacuum in the three vacuum manifolds, a thermoplastic ribbon of film running circumferentially about a portion of the debossing-perforating cylinder 555 is sequentially subjected to a first level of vacuum by manifold 561, a second level of vacuum by manifold 562, and a third level of vacuum by manifold 563. As will be described more fully hereinafter, the vacuum applied to the film by manifold 561 enables maintaining upstream tension in the film, vacuum applied by manifold 562 enables perforating the film when hot air is directed radially inwardly against the film, and vacuum applied by manifold 563 enables cooling the film to below its thermoplastic temperature and enables establishing downstream tension therein. If desired, the film contacting surface of the debossing-perforating cylinder 555 may be preheated prior to reaching vacuum manifold 562 by means well known in the art (and therefore not shown) to facilitate better conformance of plastic films comprised of flow-resistant polymers during the debossing operation. The nip 570 intermediate chill roll 566 and the soft-face roll 567 is only nominally loaded because high pressure would iron-out the three-dimensional debossments which are formed in the film in the aforementioned manner. However, even nominal pressure in nip 570 helps the vacuum applied by manifold 563 to isolate downstream tension (i.e., roll winding tension) from the debossing-perforating portion of the debossing-perforating cylinder 555, and enables the nip 570 to peel the debossed and perforated film from the debossing-perforating cylinder 555. Moreover, while vacuum drawn ambient air passing through the film into manifold 563 will normally cool the film to below its thermoplastic temperature, the passage of coolant through the chill roll as indicated by arrows 573, 574 in FIG. 11 will enable the apparatus to handle thicker films or be operated at higher speeds.

To summarize, the first vacuum manifold 561, and the third vacuum manifold 563 located within the debossing-perforating cylinder 555 enable maintaining substantially constant upstream and downstream tension, respectively, in a running ribbon of film while the intermediate portion of the film adjacent the second vacuum manifold 562 within the debossing-perforating cylinder 555 is subjected to tension vitiating heat and vacuum to effect debossing and perforating of the film.

Referring again to FIG. 11, the constant tension film supply means 541 and the constant tension film forwarding and winding means 545 may, if desired, be substantially identical to and function substantially identically to the corresponding portions of the apparatus shown and described in U.S. Pat. No. 3,674,221 issued to Riemersma on Jul. 4, 1972 and which is hereby incorporated herein by reference. The debossing and perforating means 543 comprises the rotatably mounted debossing-perforating cylinder 555, means (not shown) for rotating the cylinder 555 at a controlled peripheral velocity, the non-rotating triplex vacuum manifold assembly 556 inside the debossing-perforating cylinder 555, means (not shown) for applying controlled levels of vacuum inside the three vacuum manifolds 561, 562 and 563 comprising the triplex manifold assembly 556, and hot air jet means 559.

The debossing-perforating cylinder 555 may be constructed by generally following the teachings of U.S. Pat. No. 4,151,240 issued to Lucas et al. on Apr. 24, 1979 and incorporated herein by reference, but substituting a tubular laminate forming surface of the present invention for the perforated tubular forming surface disclosed therein.

While a preferred application of the disclosed photo-etched laminate structure is in a vacuum film forming operation as generally outlined in the aforementioned commonly assigned patent issued to Lucas et al., it is anticipated that photoetched laminate forming structures of the present invention could be employed with equal facility to directly form a three-dimensional plastic structure of the present invention. Such a procedure would involve applying a heated fluid plastic material, typically a thermoplastic resin, directly to the forming surface applying a sufficiently great pneumatic differential pressure to the heated fluid plastic material to cause said material to conform to the image of the perforate laminate forming surface, allowing the fluid material to solidify, and thereafter removing the three-dimensional plastic structure from the forming surface.

Another preferred method for converting a ribbon of thermoplastic film into a three-dimensional structure of the type herein disclosed is by applying a high pressure fluid jet comprised of water or the like against one surface of the film, preferably while applying a vacuum adjacent the opposite surface of the film. Such methods are described in greater detail in commonly assigned U.S. Pat. Nos. 4,609, 518 issued to Curro et al. on Sep. 2, 1986; 4,629,643 issued to Curro et al. on Dec. 16, 1986; 4,637,819 issued to Ouellette et al. on Jan. 20, 1987; 4,681,793 issued to Linman et al. on Jul. 21, 1987; 4,695,422 issued to Curro et al. on Sep. 22, 1987; 4,778,644 issued to Curro et al. on Oct. 18, 1988; 4,839,216 issued to Curro et al. on Jun. 13, 1989; and 4,846,821 issued to Lyons et al. on Jul. 11, 1989, each of said patents being incorporated herein by reference.

In the event it is desired to produce webs of the present invention wherein all or a predetermined portion of the web is capable of preventing fluid transmission, e.g., for use as backsheets on disposable absorbent articles, it is feasible to perform the debossing operation without causing rupture of the web in its second surface. Commonly assigned U.S. Pat. No. 4,395,215 issued to Bishop on Jul. 26, 1983 and commonly assigned U.S. Pat. No. 4,747,991 issued to Bishop on May 31, 1988, each of which are hereby incorporated herein by reference, fully disclose how to construct tubular forming structures which are capable of producing three-dimensionally expanded films which are uniformly debossed, but apertured only in predetermined areas. Such films may also be useful in product applications wherein the fluid target zone is very well defined, and fluid-perviousness is desired only in the fluid target zone.

In the case of fluid impervious films of the present invention it is anticipated that the present technology could, if desired, be incorporated in suitably reinforced film embossing rolls and the like, provided only that the embossing pressures to which the rolls will ultimately be subject are not so great as to destroy the particular three-dimensional pattern established by the laminate embossing surface. A resilient back-up roll could, if desired, be utilized in such an embossing operation to avoid damaging the laminate embossing surface. It is even further anticipated that laminate forming surfaces of the present invention may find utility in applications other than plastic film forming.

While particular embodiments of the present invention have been illustrated and described, it will be obvious to those skilled in the art that various changes and modifications can be made without departing from the spirit and scope of the invention, and it is intended to cover in the appended claims all such modifications that are within the scope of this invention.

What is claimed is:

1. A resilient three-dimensional web having a first surface in a first plane and a second surface in a second plane, said web exhibiting a fiber-like appearance and tactile impression, said web being comprised of a fluid-impervious plastic material, said first surface having a multiplicity of apertures therein, each of said apertures being defined by a multiplicity of intersecting fiber-like elements interconnected to one another in the first plane, each of said fiber-like elements exhibiting a substantially uniform generally upwardly concave-shaped cross-section along its length, said cross-section comprising a pair of convergent substantially linear portions which intersect one another at an end to form a single vertex in said first plane, said vertex defining an angle theta (θ) such that theta (θ) is from about 20° to about 140°, said cross-section further comprising a sidewall portion joined to a free end of each of said linear portions, said sidewall portions extending generally in the direction of said second surface of said web, said intersecting substantially linear portions and said intersecting sidewall portions being interconnected to one another, respectively, intermediate said first and second surfaces of said web, said interconnected sidewall portions terminating substantially concurrently with one another in the second plane of said web.

2. The resilient three-dimensional web of claim 1, wherein said web comprises a topsheet on an absorbent article.

3. The resilient three-dimensional web of claim 1, wherein said second surface of said web contains a multiplicity of apertures and said interconnected sidewall portions of said fiber-like elements terminate substantially concurrently with one another in said apertures in the second surface of said web.

4. The resilient three-dimensional web of claim 3, wherein theta (θ) is from about 40° to about 120°.

5. The resilient three-dimensional web of claim 3, wherein said fluid-impervious plastic material comprises a thermoplastic film.

6. The resilient three-dimensional web of claim 3, wherein theta (θ) is from about 60° to about 100°.

7. The resilient three-dimensional web of claim 6, wherein the capillaries of said network connecting said aperatures in said first surface of said web exclusively with the corresponding apertures in said second surface of said web are of decreasing cross-section in the direction of said second surface, thereby promoting rapid transmission of fluid deposited on said apertures in said first surface to the corresponding apertures in said second surface without lateral transmission of said fluid between adjacent capillaries of said network.

8. The resilient three-dimensional web of claim 3, wherein said interconnected substantially linear portions and said interconnected sidewall portions form a discrete capillary network connecting each of said apertures formed by said multiplicity of intersecting fiber-like elements in said first surface of said web exclusively with a corresponding aperture defined by said interconnected sidewall portions in said second surface of said web.

9. The resilient three-dimensional web of claim 8, wherein the capillaries of said network are of non-uniform cross-section along their length.

10. The resilient three-dimensional web of claim 3, wherein at least a portion of said fiber-like elements are substantially straight along a portion of their length.

11. The resilient three-dimensional web of claim 10, wherein at least a portion of said fiber-like elements are substantially straight along their entire length.

12. A resilient three-dimensional web having a first surface in a first plane and a second surface in a second plane, said web exhibiting a fiber-like appearance and tactile impression, said web being comprised of a fluid-impervious plastic material, said first surface having a multiplicity of apertures therein, each of said apertures being defined by a multiplicity of primary intersecting fiber-like elements interconnected to one another in the first plane of said web, each of said primary fiber-like elements exhibiting a substantially uniform generally upwardly concave-shaped cross-section along its length, said cross-section comprising a pair of convergent substantially linear portions which intersect one another at an end to form a single primary vertex in said first plane, said primary vertex defining a angle theta (θ) such that theta (θ) is from about 20° to about 140°, said cross-section further comprising a primary sidewall portion joined to a free end of each of said primary linear portions, said primary sidewall portions extending generally in the direction of said second surface of said web, said primary intersecting substantially linear portions and said primary intersecting sidewall portions being interconnected to one another respectively intermediate said first and said second surfaces of said web, said interconnected primary sidewall portions being further connected to at least one secondary intersecting fiber-like element exhibiting a substantially uniform generally upwardly concave-shaped cross-section along its length, said cross-section of said secondary element comprising a pair of secondary convergent substantially linear portions which intersect one another at an end to form a single secondary vertex in a plane intermediate said first and second surfaces of said web, said secondary vertex defining an angle theta (θ) such that theta (θ) is from about 20° to about 140°, said cross-section further comprising a secondary sidewall portion joined to a free end of each said secondary linear portions, said secondary sidewall portions extending generally in the direction of said second surface of said web, said interconnected primary and secondary sidewall portions terminating substantially concurrently with one another in the second plane of said web.

13. The resilient three-dimensional web of claim 12, wherein said web comprises a topsheet on an absorbent article.

14. The resilient three-dimensional web of claim 12, wherein said second surface of said web contains a multiplicity of apertures and said interconnected primary and secondary sidewall portions of said fiber-like elements terminate substantially concurrently with one another in said apertures in the second surface of said web.

15. The resilient three-dimensional web of claim 14, said secondary fiber-like elements forming a discrete capillary network connecting each of said apertures defined by said multiplicity of intersecting primary fiber-like elements in said first surface of said web exclusively with a multiplicity of said apertures formed in said second surface of said web by said interconnected primary and secondary sidewall portions of said fiber-like elements.

16. The resilient three-dimensional web of claim 15, wherein the capillaries of said network are of non-uniform cross-section along their length.

17. The resilient three-dimensional web of claim 16, wherein the capillaries of said network connecting each of said apertures in said first surface of said web exclusively with the corresponding multiplicity of apertures in said second surface of said web are of decreasing cross-section in the direction of said second surface, thereby promoting rapid transmission of fluid deposited on each of said apertures in said first surface to the corresponding multiplicity of apertures in said second surface without lateral transmission of said fluid between adjacent capillaries of said network.

18. The resilient three-dimensional web of claim 14, wherein at least a portion of said primary fiber-like elements are substantially straight along a portion of their length.

19. The resilient three-dimensional web of claim 18, wherein at least a portion of said secondary fiber-like elements are substantially straight along a portion of their length.

20. A resilient three-dimensional web having a first surface in a first plane and a second surface in a second plane, said web exhibiting a fiber-like appearance and tactile impression, said web being comprised of a fluid-impervious plastic material, said first surface having a multiplicity of apertures therein, each of said apertures being defined by a multiplicity of intersecting fiber-like elements interconnected to one another in the first plane, each of said fiber-like elements exhibiting a substantially uniform generally upwardly concave-shaped cross-section along its length, said cross-section comprising a pair of convergent substantially linear portions which intersect one another at an end to form a single vertex in said first plane, said vertex defining an angle theta ($\theta$) such that theta ($\theta$) is from about 20° to about 140°, said linear portions each representing a cross-section through a substantially planar surface and said vertex representing a line of intersection of said planar surfaces such that an upper surface of each fiber-like element forms a dihedral angle, said cross-section further comprising a sidewall portion joined to a free end of each of said linear portions, said sidewall portions extending generally in the direction of said second surface of said web, said intersecting substantially linear portions and said intersecting sidewall portions being interconnected to one another, respectively, intermediate said first and second surfaces of said web, said interconnected sidewall portions terminating substantially concurrently with one another in the second plane of said web.

* * * * *